United States Patent
Van Breugel et al.

(10) Patent No.: US 10,093,608 B2
(45) Date of Patent: Oct. 9, 2018

(54) METHOD FOR MANUFACTURING SUCCINIC ACID

(71) Applicant: PURAC BIOCHEM B.V., AC Gorinchem (NL)

(72) Inventors: Jan Van Breugel, AC Gorinchem (NL); Peter Paul Jansen, AC Gorinchem (NL); Jose Maria Vidal Lancis, AC Gorinchem (NL); Tanja Dekic Zivkovic, AC Gorinchem (NL); Adriaan Dirk Kon, AC Gorinchem (NL)

(73) Assignee: PURAC BIOCHEM B.V. (NL)

( * ) Notice: Subject to any disclaimer, the term of this patent is extended or adjusted under 35 U.S.C. 154(b) by 0 days.

(21) Appl. No.: 15/743,842

(22) PCT Filed: Jul. 14, 2016

(86) PCT No.: PCT/EP2016/066806
§ 371 (c)(1),
(2) Date: Jan. 11, 2018

(87) PCT Pub. No.: WO2017/009433
PCT Pub. Date: Jan. 19, 2017

(65) Prior Publication Data
US 2018/0194706 A1    Jul. 12, 2018

(30) Foreign Application Priority Data
Jul. 14, 2015  (EP) .................................... 15176659

(51) Int. Cl.
| | | |
|---|---|---|
| *C07C 51/02* | (2006.01) | |
| *C07C 51/43* | (2006.01) | |
| *C07C 51/47* | (2006.01) | |
| *C07C 51/48* | (2006.01) | |
| *C12P 7/46* | (2006.01) | |
| *C01B 7/03* | (2006.01) | |
| *C01F 5/10* | (2006.01) | |
| *C07C 55/10* | (2006.01) | |

(52) U.S. Cl.
CPC .............. *C07C 55/10* (2013.01); *C01B 7/035* (2013.01); *C01F 5/10* (2013.01); *C07C 51/02* (2013.01); *C07C 51/43* (2013.01); *C07C 51/47* (2013.01); *C07C 51/48* (2013.01); *C12P 7/46* (2013.01)

(58) Field of Classification Search
CPC ......... C07C 51/02; C07C 51/43; C07C 51/47; C07C 51/48; C07C 55/10; C12P 7/46
See application file for complete search history.

(56) References Cited

FOREIGN PATENT DOCUMENTS

| | | | |
|---|---|---|---|
| WO | 2008/010373 A1 | 1/2008 | |
| WO | WO-2008010373 A1 * | 1/2008 | ............ C07C 51/02 |
| WO | 2013/025105 A1 | 2/2013 | |
| WO | WO-2013025107 A1 * | 2/2013 | ............ C07C 51/02 |
| WO | 2015/000956 A1 | 1/2015 | |

OTHER PUBLICATIONS

International Search Report and Written Opinion in International Application No. PCT/EP2016/066806, dated Oct. 10, 2016.

* cited by examiner

*Primary Examiner* — Paul A Zucker
(74) *Attorney, Agent, or Firm* — J. A. Lindeman & Co., PLLC

(57) ABSTRACT

The invention pertains to a method for preparing succinic acid which comprises providing an aqueous magnesium succinate solution to an acidification step, wherein the magnesium succinate solution is acidified by the addition of hydrogen chloride, thereby obtaining an aqueous solution comprising succinic acid and magnesium chloride and subjecting the aqueous solution comprising succinic acid and magnesium chloride derived from the acidification step to a treatment step with active carbon followed by precipitating succinic acid from an aqueous mixture comprising succinic acid and magnesium chloride resulting from the active carbon treatment step in a precipitation step to form solid succinic acid. It has been found that the method according to the invention leads to succinic acid crystals with better properties than a comparable method wherein no active carbon treatment is used.

20 Claims, 3 Drawing Sheets

METHOD FOR MANUFACTURING SUCCINIC ACID

The invention is directed to a method for manufacturing succinic acid, in particular succinic acid in crystalline form.

Succinic acid, also known as butanedioic acid, has many industrial applications. It is used, e.g., in the food and beverage industry. It is also used as a starting material for the production of succinate esters, which can e.g., be used as starting material for the production of butane diol, which in turn can be used as monomer in the manufacture of plastics.

An attractive way to manufacture succinic acid is through a fermentation process, wherein a carbon source is fermented by means of a microorganism to form succinic acid. The liquid wherein the carbohydrate source is fermented is called the fermentation broth or the fermentation medium. The formation of succinic acid during fermentation will result in a decrease of the pH of the fermentation broth. Since such a decrease in pH can damage the microorganism's metabolic process, it is common practice to add a neutralizing agent, i.e. a base, to the fermentation medium, to keep the pH in a range where the microorganism can perform. As a result, the succinic acid produced will be present in the fermentation medium in the form of a succinate salt, with the cation of the salt being the cation of the base added during fermentation.

To recover the succinic acid from the fermentation broth after fermentation, downstream processing is required. In such processing, the succinate salt in the fermentation broth needs to be converted into succinic acid. Also, the succinic acid (or succinate if not yet converted) needs to be isolated from the fermentation broth. Since a fermentation broth comprises many compounds, including significant amounts of biomass (such as microorganisms) and salt (originating from the neutralizing agent), recovering and isolating succinic acid can be rather complex.

WO2013025105 describes a method for a method for preparing succinic acid, which method comprises the steps of providing magnesium succinate, in particular though a fermentation process, acidifying the magnesium succinate with hydrogen chloride to obtain a solution comprising succinic acid and magnesium chloride, concentrating the solution comprising succinic acid and magnesium chloride, and precipitating succinic acid from the solution. The magnesium chloride solution may be subjected to a thermal decomposition step to form hydrogen chloride and magnesium oxide, with the hydrogen chloride being recycled to the acidification step.

It has been found, however, that the process as described in WO2013025105 requires further improvement. More specifically it has been found that the precipitation of succinic acid from the magnesium chloride solution is to be improved. It has been found that in the process of WO2013025105 the succinic acid precipitates in the form of needle-like crystals, which are difficult to isolate. This leads to a product which is difficult to isolate by filtration, difficult to wash, and wherein yield and purity of the isolated product can be improved.

It has been found that the product properties of the process described in WO2013025105 can be solved by the process according to the invention.

Accordingly, the present invention pertains to a method for preparing succinic acid comprising the steps of
providing an aqueous magnesium succinate solution to an acidification step, wherein the magnesium succinate solution is acidified by the addition of hydrogen chloride, thereby obtaining an aqueous solution comprising succinic acid and magnesium chloride;
subjecting an aqueous solution comprising succinic acid and magnesium chloride derived from the acidification step to a treatment step with active carbon,
precipitating succinic acid from an aqueous mixture comprising succinic acid and magnesium chloride resulting from the active carbon treatment step in a precipitation step to form solid succinic acid and a magnesium chloride solution,
separating the solid succinic acid from the magnesium chloride solution
subjecting the magnesium chloride solution to a thermal decomposition at a temperature of at least 300° C., thereby decomposing the magnesium chloride to magnesium oxide and hydrogen chloride, and
recycling the hydrogen chloride generated in the thermal decomposition step to the acidification step.

It has been found that the provision of a treatment step with active carbon at the specific location after the acidification step and before the precipitation step leads to a precipitation process with improved properties. More in particular, it has been found that the process according to the invention yields block-shaped crystals, rather than the needle-like crystals which are formed in the method of WO2013/025105. The block-shaped crystals are easier to isolate, e.g., by filtration. This results in easier processing and an improved yield. The crystals are also easier to wash, resulting in a final product with a lower chlorine content. The crystals are also larger.

The method according to the invention will be discussed in more detail below.

The method according to the invention will also be illustrated by reference to the Figures, without being limited thereto or thereby.

Figure 1:
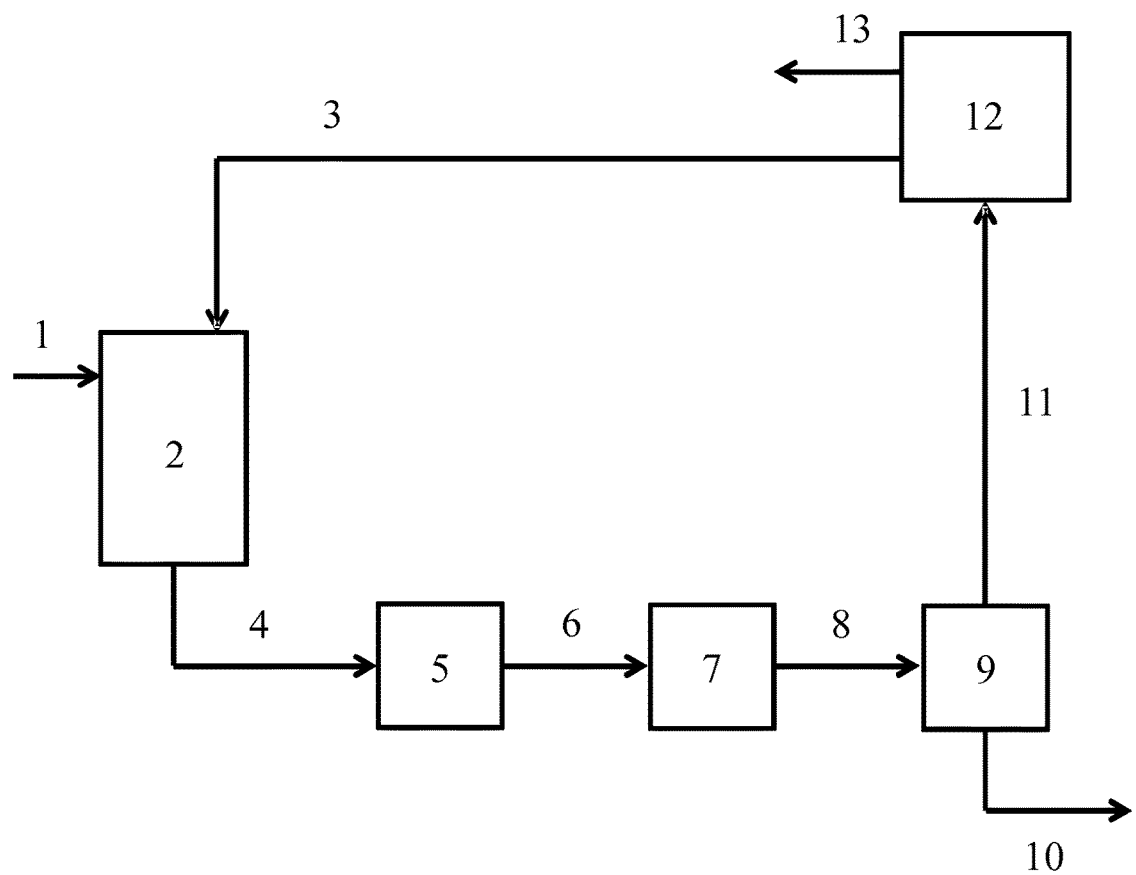
FIG. 1 illustrates a first embodiment of the present invention.

In FIG. 1, an aqueous magnesium succinate solution is provided through line (1) to acidification reactor (2), where it is contacted with HCl, provided through line (3). An aqueous solution comprising succinic acid and magnesium chloride is withdrawn through line (4), and provided to carbon treatment step (5). The solution withdrawn from carbon treatment step (5) is provided through line (6) to precipitation reactor (7). In precipitation reactor (7) a slurry of solid succinic acid is formed which is provided through line (8) to separator (9). In separator (9) a solid succinic acid product is separated, e.g., by filtration, and withdrawn through line (10). The magnesium chloride solution is withdrawn through line (11), and provided to thermal decomposition step (12). In thermal decomposition step (12), the magnesium chloride solution is decomposed to form HCl gas and solid MgO. The solid MgO is withdrawn through line (13), and may, if so desired, be provided directly or after conversion into magnesium hydroxide or magnesium carbonate or bicarbonate as base to a fermentation reactor (not shown), in particular a fermentation reactor wherein succinic acid is produced by fermentation of a carbon source. The HCl is provided, directly or after dissolution in an aqueous liquid, to the acidification reactor (2).

The invention starts out with the provision of an aqueous magnesium succinate solution to an acidification step.

The aqueous magnesium succinate solution can be derived from various sources. In one embodiment, the aqueous magnesium succinate solution is derived from a fermentation process. In such a fermentation process, a carbon source is fermented in a fermentation medium by means of a microorganism capable of producing succinic acid to form succinic acid, and at least part of the succinic acid is neutralized with a magnesium base selected from magnesium oxide, magnesium hydroxide, magnesium carbonate, and magnesium bicarbonate. Once the fermentation has been completed, the fermentation medium comprising dissolved magnesium succinate will generally be submitted to a biomass removal step, by methods known in the art. The resulting magnesium succinate solution can be provided as starting material in the process according to the invention. Fermentation processes are known in the art, and require no further elucidation here.

The magnesium succinate solution provided to the acidification step generally has a magnesium succinate concentration of 5-50 wt. %. Within this range, higher concentrations are preferred, because this results in an improved succinic acid yield in the precipitation step. On the other hand, higher concentrations may result in crystallization of magnesium succinate or an uncontrolled process. The suitable magnesium succinate concentration will also depend on the concentration of the HCl. In practice, a magnesium succinate concentration of 15-50 wt. %, in particular 15-40 wt. % may be preferred. For higher concentrations it may be necessary to have the magnesium succinate solution at a higher temperature to prevent precipitation. It may thus be preferred for the solution to be at a temperature of 20-140° C., in particular 60-120° C., more in particular 80-120° C. As will be evident to the skilled person, where the temperature of the solution is above 100° C., the solution should be under a pressure which is sufficiently high to ensure that the solution is in the liquid phase.

The concentration of the magnesium succinate solution derived from a fermentation process generally is in the range of 1-17 wt. %, in particular in the range of 5-14 wt. %. It may be preferred to subject the magnesium succinate solution before acidification to a concentration step, wherein water is removed by evaporation, if so desired at increased temperature and/or decreased pressure, so that a magnesium succinate solution with a magnesium succinate concentration in the desired range is obtained.

In the acidification step, the magnesium succinate solution is contacted with hydrogen chloride (HCl). HCl acidification may for example be conducted with an aqueous HCl solution or HCl gas. Where a HCl solution is used, it preferably has HCl concentration which is relatively high, to prevent the addition of unnecessary water to the system. The HCl solution therefore preferably comprises at least 5 wt. %, more preferably at least 10 wt. % and even more preferably at least 20 wt. % HCl.

The use of a gaseous HCl stream is also possible. In one embodiment the gaseous HCl stream is derived from the thermal decomposition of magnesium chloride. This will be discussed in more detail below.

The amount of HCl added in the acidification step is governed by the amount necessary to convert the magnesium succinate into succinic acid. It may be preferred that the ratio of the total amount of HCl provided to the process and the total amount of magnesium succinate provided to the process is such that there is a slight excess of HCl. For example, the excess of HCl used may be such that the final aqueous mixture comprising succinic acid and magnesium chloride has a pH 2 or lower, preferably a pH of 1-2.

The temperature of the HCl may vary within wide ranges, e.g., between 5 and 130° C., also dependent on whether the HCl is provided in gaseous form, or in the form of an aqueous solution. Higher temperatures may be preferred, because the acidification reaction preferably is carried out at a higher temperature. Further, if the HCl is derived from the thermal decomposition of magnesium chloride, as will be discussed in more detail below, it will of itself have a higher temperature. A suitable temperature for the HCl may be in the range of 50-120° C., in particular 70-120° C.

The acidification step may be carried out in a single step, or in more than one step, as desired.

The product of the acidification step is an aqueous solution comprising succinic acid and magnesium chloride.

In the process according to the invention a carbon treatment step is carried out after the acidification step. The carbon treatment is thus performed on the aqueous solution comprising succinic acid and magnesium chloride as it is obtained after the acidification step (optionally followed by a concentration step), wherein this solution preferably comprises succinic acid in a concentration of at least 10 wt. %, more preferably at least 15 wt. % and magnesium chloride in a concentration of at least 10 wt. %, more preferably at least 15 wt. %.

To prevent interference with the carbon treatment, the concentrations of succinic acid and magnesium chloride in the aqueous solution subjected to the carbon treatment are required to be such that these compounds are fully dissolved. This can be achieved by a suitable selection of the succinic acid concentration, magnesium chloride concentration, pH, and temperature. It is not the objection of the present invention to have the acidification step or the optional concentration step thereafter carried in such manner that a substantial amount of succinic acid (a substantial amount preferably being an amount of at least 10 wt.-%, based on the total amount of succinic acid in the acidified and optionally concentrated aqueous solution comprising succinic acid and magnesium chloride) precipitates after which the precipitated crystals —either directly or after having been separated first from the liquid—are re-dissolved again (by for example addition of a diluent such as for example water) and are then treated with carbon. In this context it is particularly preferred that, by controlling the process parameters such a the concentration of magnesium chloride, the concentration of succinic acid, the pH and the temperature, the acidification and the optional concentration step thereafter are carried in such manner that at most 5 wt.-%, more preferably at most 1 wt.-% and even more preferably at most 0.1 wt.-% of the succinic acid precipitates from the acidified and optionally concentrated solution before the carbon treatment is performed, these amounts again being based on the total amount of succinic acid in the acidified and optionally concentrated aqueous solution comprising succinic acid and magnesium chloride. According to a particularly preferred embodiment of the process according to the present invention the acidification and the optional concentration step thereafter are carried in such manner that almost no succinic acid at all precipitates from the acidified and optionally concentrated solution before the carbon treatment is performed.

In one embodiment, the solution as obtained from the acidification step (or optionally the solution that is obtained therefrom after a subsequent concentration step), that is subjected to the carbon treatment, has a succinic acid concentration of at least 10 wt. %, in particular at least 15 wt. %. Higher concentrations, e.g., at least 18 wt. % can also be applied, when elevated temperatures are used, e.g., at least 60° C., in particular at least 75° C., or even at least 85° C. For even higher concentrations, e.g., at least 20 wt. %, still higher temperatures may be required, e.g., at least 90° C., or at least 100° C. When working above 100° C. it will be necessary to work under pressure to ensure that the solution is in the liquid phase. As a maximum temperature a value of 180° C. may be mentioned. The upper limit for the succinic acid concentration will depend on the temperature, pH, and magnesium chloride concentration of the solution. As a general maximum a value of 25 wt. % may be mentioned. It is within the scope of the skilled person to select a suitable succinic acid concentration.

The magnesium chloride concentration of the aqueous mixture generally is in the range of 10-25 wt. %, more in particular 15-25 wt. %, dependent on the magnesium succinate concentrations in the previous solution. As magnesium chloride has a relatively high solubility, the magnesium chloride concentration is less critical than the succinic acid concentration.

The solution generally has a pH of below 2, in particular between 1 and 2.

If so desired, a concentration step can be carried out on the aqueous solution comprising succinic acid and magnesium chloride after the acidification step and before the carbon treatment, as long as the above requirements as to solubility of the succinic acid and magnesium chloride during the carbon treatment step are met. The concentration step can be carried out by methods known in the art, and will generally involve removal of water at elevated pressure and/or reduced temperature.

It has been found that the performance of the carbon treatment at this particular location in the process results in improved properties of the solid succinic acid, in particular with an improved crystal structure.

The carbon treatment can be carried out by contacting the product of the acidification step, whether or not after a further concentration step, with active carbon. This can be done by methods known in the art, e.g., by passing the solution through a column comprising active carbon, or by adding active carbon to the solution and mixing it through the medium followed by removing it, e.g., by filtration, or by other suitable methods. Contacting time may vary within wide ranges. It is, e.g., in the range of 1 minute to 24 hours, in particular 10 minutes to 3 hours, more specifically 60 minutes to 150 minutes.

The temperature at which the carbon treatment is carried out is not critical, as long as it is sufficiently high that succinic acid does not precipitate from the solution. This will also depend on the succinic acid concentration. The temperature may suitable be in the range of 5-150° C., in particular in the range of 20-130° C., more in particular in the range of 50-120° C.

The amount of carbon may vary within wide ranges, e.g., between 0.01 and 10 gram carbon per liter of aqueous solution to be treated, more in particular between 0.1 and 2 gram carbon per liter of aqueous solution to be treated.

The carbon used in the carbon treatment is activated carbon. The activated carbon can be in the form of particles, e.g., with a diameter of 0.2-3 mm. It can also be in the form of powder.

Activated carbon is known in the art. It is commercially available and requires no further elucidation here.

The carbon treatment step generates an aqueous solution comprising succinic acid and magnesium chloride, which is provided to a precipitation step.

If so desired, a concentration step can be carried out after the carbon treatment and before the concentration step, generally by the removal of water by evaporation. A higher concentration of succinic acid in the solution will increase the efficiency of the succinic acid precipitation.

It may be that during the concentration step some succinic acid already precipitates. This does not interfere with the further precipitation step. The amount of water removed in the concentration step should be selected such that no magnesium chloride precipitates. However, due to the high solubility of magnesium chloride this can easily be avoided.

The product provided to the precipitation step may thus be an aqueous solution wherein succinic acid and magnesium chloride are in the dissolved state. It may also be an aqueous slurry comprising magnesium chloride in the dissolved state and succinic acid which is partially in the dissolved state and partially in the solid state. In the present specification the term aqueous mixture is intended to encompass both the solution and the slurry.

It may be preferred for the aqueous mixture provided to the precipitation step to have a succinic acid concentration of at least 15 wt. %, in particular at least 18 wt. %, more in particular at least 20 wt. %. Higher succinic acid concentrations are advantageous because they result in a higher succinic acid yield in the precipitation step. As a general maximum a value of 30 wt. % may be mentioned. Concentrations higher than 30 wt. % are difficult to obtain. It may be preferred for the succinic acid concentration to be at most 25 wt. %.

The magnesium chloride concentration of the aqueous mixture generally is in the range of 10-25 wt. %, more in particular 15-25 wt. %, dependent on the magnesium succinate concentrations in the previous solution.

As indicated above, the mixture generally has a pH of below 2, in particular between 1 and 2.

In the precipitation step, succinic acid is precipitated from the solution, resulting in the formation of succinic acid in solid form, which can be separated from the magnesium chloride solution.

In the precipitation step, succinic acid is precipitated from the aqueous mixture via methods known in the art, including decreasing the temperature of the mixture, e.g., via natural cooling crystallization, controlled cooling crystallization, or flash-cooling crystallisation, removal of water from the mixture to increase the succinic acid concentration, and adding an antisolvent. The latter embodiment may be less preferred because it encompasses the addition of further components to the system.

In one embodiment, where the aqueous mixture already contains some succinic acid in solid form generated during the precipitation step, it may be advantageous to first increase the temperature of the mixture to a value at which all succinic acid is present in solution, and then decrease the temperature to initiate crystallization of succinic acid. In one embodiment, the solution from which succinic acid is to be precipitated is cooled from a temperature of at least 35° C. to a temperature of less than 30° C., preferably from a temperature of at least 40° C. to a temperature of less than 25° C. Higher temperature differences make it possible to increase the yield of succinic acid precipitate.

The precipitated succinic acid can be separated from the magnesium chloride solution by methods known in the art. Suitable methods include filtration techniques, also including membrane filtration, sedimentation techniques, techniques based on gravity separation such as decantation, and techniques comprising a centrifugation step. Combinations of various methods, e.g. centrifugation followed by decantation can also be used.

As indicated before, the crystals obtained by the method according to the invention have a regular block shape, which allows them to be separated by filtration and washed with ease. Further, the crystals obtained by the method according to the invention can be washed to a much lower chloride content than the needle-shaped crystals which are obtained using the method of WO2013/025105.

The magnesium chloride solution resulting from the separation step may be processed as desired. In one embodiment, if there are still significant amounts of succinic acid remaining in the magnesium chloride solution, one or more further succinic acid precipitation steps can be carried out, followed by one or more further separation steps. These steps can be carried out by in the manner discussed above.

The magnesium chloride solution derived from the step of separating the solid succinic acid from the magnesium chloride solution is provided to a thermal decomposition step. In the thermal decomposition step, magnesium chloride is decomposed at a temperature of at least 300° C., in particular in the range of 350 to 600° C. in the presence of water to form magnesium oxide in solid form, and hydrogen chloride in gaseous form. Suitable thermal decomposition methods are known in the art and require no further elucidation here. They are, e.g., described in WO2013/025105, WO2015/00956, and non-prepublished PCT application PCT/EP2015/056895.

The hydrogen chloride generated in the thermal decomposition step is recycled to the acidification step. The HCl can be provided in gaseous form or after dissolution in water to form an aqueous HCl solution.

In one embodiment the starting aqueous solution of magnesium succinate is derived from a fermentation process. In such a fermentation process, a carbon source is fermented in a fermentation medium by means of a micro-organism capable of producing succinic acid to form succinic acid, while neutralizing at least part of the succinic acid with a magnesium base selected from magnesium oxide, magnesium hydroxide, magnesium carbonate, and magnesium bicarbonate. Once the fermentation has been completed, the fermentation medium comprising dissolved magnesium succinate will generally be submitted to a biomass removal step, by methods known in the art. The resulting magnesium succinate solution can be provided as starting material in the process according to the invention, whether or not after having been subjected to a concentration step to remove water.

Fermentation processes are known in the art, and require no further elucidation here.

In addition to HCl, the thermal decomposition step also generates magnesium oxide. This can be processed as desired. In one embodiment the magnesium oxide generated in the thermal decomposition step is provided as neutralizing agent to a fermentation process generating succinic acid, either directly, or after conversion into magnesium hydroxide, magnesium carbonate, or magnesium bicarbonate.

In one embodiment the present invention pertains to an integrated process comprising the steps of
subjecting a carbon source to a fermentation step to form succinic acid, which fermentation step comprises the steps of fermenting a carbon source by means of a micro-organism capable of producing succinic acid in a fermentation broth to form succinic acid and neutralizing at least part of the succinic acid by adding a magnesium base selected from magnesium oxide, magnesium hydroxide, magnesium carbonate, and magnesium bicarbonate, thereby obtaining a magnesium succinate solution, providing the aqueous magnesium succinate solution, optionally after a biomass removal step and/or a concentration step, to an acidification step, wherein the magnesium succinate solution is acidified by the addition of hydrogen chloride, thereby obtaining an aqueous solution comprising succinic acid and magnesium chloride;

subjecting an aqueous solution comprising succinic acid and magnesium chloride derived from the acidification step to a treatment step with active carbon, precipitating succinic acid from an aqueous mixture comprising succinic acid and magnesium chloride resulting from the active carbon treatment step in a precipitation step to form solid succinic acid and a magnesium chloride solution, separating the solid succinic acid from the magnesium chloride solution subjecting the magnesium chloride solution to a thermal decomposition at a temperature of at least 300° C., thereby decomposing the magnesium chloride to magnesium oxide and hydrogen chloride, and recycling the hydrogen chloride generated in the thermal decomposition step to the acidification step and optionally providing the magnesium oxide as neutralising agent to the fermentation step, as such or after conversion to magnesium hydroxide, magnesium carbonate, or magnesium bicarbonate, The various steps of the process according to this embodiment of the invention may be carried out as described in more detail above.

It will be evident to the skilled person that the various aspects of the present invention which are described above in different paragraphs may be combined, unless they are mutually exclusive.

The invention and certain embodiments of the inventions are illustrated by the following examples and/or embodiments, without being limited thereto or thereby.

EXAMPLE 1

Example 1a

Method According to the Invention

An aqueous magnesium succinate solution with a magnesium succinate concentration of 22.5 wt. % was acidified by the addition of HCl. HCl was provided in the form of a HCl-containing gas. The HCl gas stream was derived from a thermal decomposition step wherein a magnesium chloride solution derived from a succinate precipitation step was subjected to a thermal decomposition step. The amount of HCl was selected such that the pH of the resulting aqueous solution was 1.1. The resulting acidified solution had a succinic acid concentration of 19 wt. % and a magnesium chloride concentration of 14 wt. %. The solution had a temperature of 92° C.

The aqueous solution was subjected to a carbon treatment by providing it to a column packed with active carbon, at a flow of 1 bed volume per hour.

The aqueous solution derived from the carbon treatment was subjected to a precipitation step wherein the solution was allowed to cool down to room temperature, without additional cooling, while stirring with a magnetic stirrer.

Figure 2:
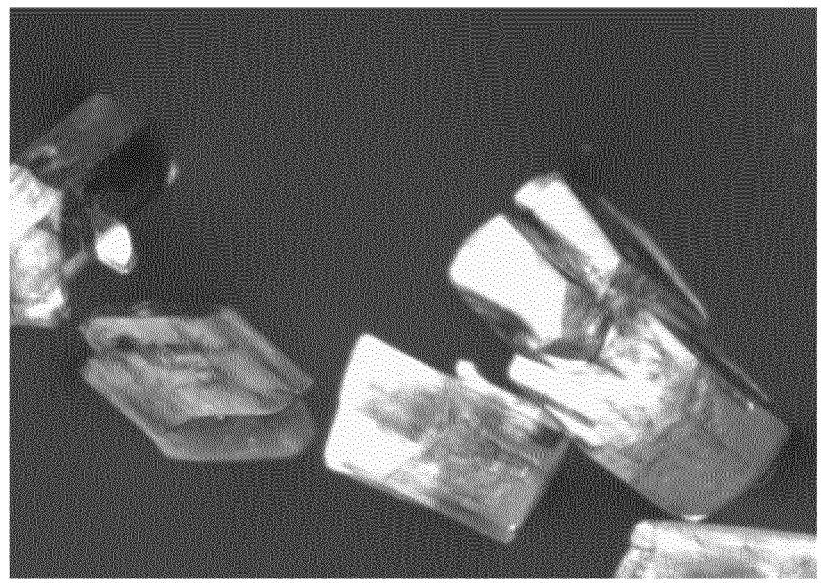
FIG. 2 shows succinic acid crystals obtained in a method according to the invention.

The precipitated succinic acid was removed by filtration. FIG. 2 is a microphotograph (degree of enlargement 50×) of the succinic acid crystals obtained.

As can be seen from FIG. 2, the crystals obtained by the method according to the invention have a regular, box-like structure. They can easily be isolated by filtration and washed to achieve high purity.

Example 1b

Comparative Method

Figure 3:
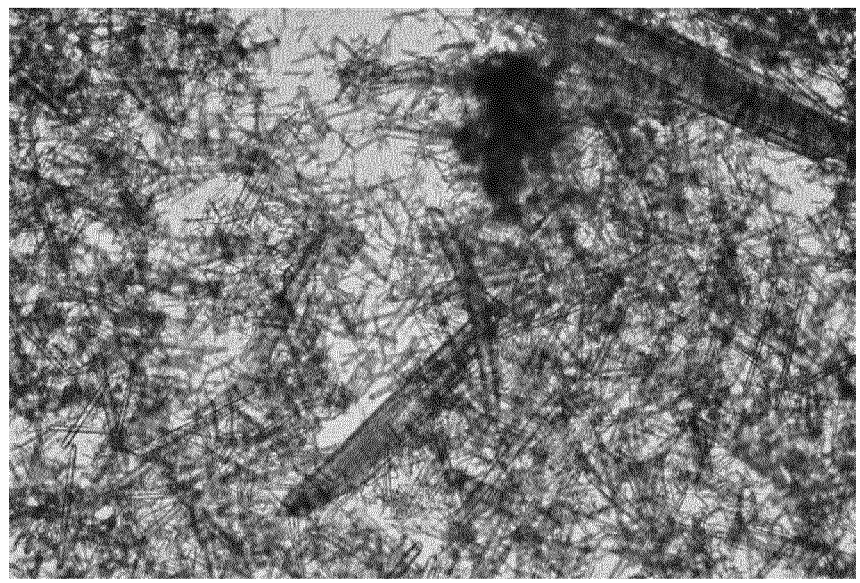
FIG. 3 shows succinic acid crystals obtained in a method not according to the invention.

Example 1a was repeated, except that no carbon treatment was carried out between the acidification step and the precipitation step. FIG. 3 is a microphotograph (degree of enlargement 10×) of the succinic acid crystals obtained. As can be seen from FIG. 3, the crystals obtained by this comparative method have a very fine, needle-like structure. This makes them difficult to isolate and wash.

The invention claimed is:

1. A method for preparing succinic acid comprising the steps of:
    providing an aqueous magnesium succinate solution to an acidification step, wherein the magnesium succinate solution is acidified by the addition of hydrogen chloride, thereby obtaining an aqueous solution comprising succinic acid and magnesium chloride;
    subjecting an aqueous solution comprising succinic acid and magnesium chloride derived from the acidification step to a treatment step with active carbon;
    precipitating succinic acid from an aqueous mixture comprising succinic acid and magnesium chloride resulting from the active carbon treatment step in a precipitation step to form solid succinic acid and a magnesium chloride solution;
    separating the solid succinic acid from the magnesium chloride solution;
    subjecting the magnesium chloride solution to a thermal decomposition at a temperature of at least 300° C., thereby decomposing the magnesium chloride to magnesium oxide and hydrogen chloride; and
    recycling the hydrogen chloride generated in the thermal decomposition step to the acidification step.

2. The method of claim 1, wherein the magnesium succinate solution provided to the acidification step has a magnesium succinate concentration of 5-50 wt. %.

3. The method of claim 1, wherein the acidification step is carried out to a pH between 1 and 2.

4. The method of claim 1, wherein the solution subjected to the carbon treatment has a succinic acid concentration of at least 10 wt. %.

5. The method of claim 4, wherein the succinic acid concentration is at least 18 wt. % at a temperature at least 60° C.

6. The method of claim 1, wherein the active carbon treatment is carried out by passing the solution through a column comprising active carbon, or by adding active carbon to the solution and mixing it through the medium followed by removing it.

7. The method of claim 1, wherein the contacting time during the active carbon treatment is in the range 1 minute to 24 hours.

8. The method of claim 1, wherein the active carbon treatment is carried out at a temperature of 50-120° C.

9. The method of claim 2, wherein the magnesium succinate solution provided to the acidification step has a magnesium succinate concentration of 15-40 wt. %.

10. The method of claim 4, wherein the solution subjected to the carbon treatment has a succinic acid concentration of at least 15 wt. %.

11. A method for preparing succinic acid comprising the steps of:
    subjecting a carbon source to a fermentation step to form succinic acid, in which the fermentation step comprises the steps of fermenting a carbon source by means of a micro-organism capable of producing succinic acid in a fermentation broth to form succinic acid and neutralizing at least part of the succinic acid by adding a magnesium base selected from magnesium oxide, magnesium hydroxide, magnesium carbonate, and magnesium bicarbonate, thereby obtaining a magnesium succinate solution;
    providing the aqueous magnesium succinate solution, optionally after a biomass removal step and/or a concentration step, to an acidification step, wherein the magnesium succinate solution is acidified by the addition of hydrogen chloride, thereby obtaining an aqueous solution comprising succinic acid and magnesium chloride;
    subjecting an aqueous solution comprising succinic acid and magnesium chloride derived from the acidification step to a treatment step with active carbon;
    precipitating succinic acid from an aqueous mixture comprising succinic acid and magnesium chloride resulting from the active carbon treatment step in a precipitation step to form solid succinic acid and a magnesium chloride solution;
    separating the solid succinic acid from the magnesium chloride solution;
    subjecting the magnesium chloride solution to a thermal decomposition at a temperature of at least 300° C., thereby decomposing the magnesium chloride to magnesium oxide and hydrogen chloride; and
    recycling the hydrogen chloride generated in the thermal decomposition step to the acidification step.

12. The method of claim 11, wherein the magnesium succinate solution provided to the acidification step has a magnesium succinate concentration of 5-50 wt. %.

13. The method of claim 11, wherein the acidification step is carried out to a pH between 1 and 2.

14. The method of claim 11, wherein the solution subjected to the carbon treatment has a succinic acid concentration of at least 10 wt. %.

15. The method of claim 14, wherein the succinic acid concentration is at least 18 wt. % at a temperature at least 60° C.

16. The method of claim 11, wherein the active carbon treatment is carried out by passing the solution through a column comprising active carbon, or by adding active carbon to the solution and mixing it through the medium followed by removing it.

17. The method of claim 11, wherein the contacting time during the active carbon treatment is in the range 1 minute to 24 hours.

18. The method of claim 11, wherein the active carbon treatment is carried out at a temperature of 50-120° C.

19. The method of claim 12, wherein the magnesium succinate solution provided to the acidification step has a magnesium succinate concentration of 15-40 wt. %.

20. The method of claim 14, wherein the solution subjected to the carbon treatment has a succinic acid concentration of at least 15 wt. %.

* * * * *